United States Patent
Briggs et al.

(10) Patent No.: US 8,558,030 B2
(45) Date of Patent: Oct. 15, 2013

(54) PROCESS FOR TELOMERIZATION OF BUTADIENE

(75) Inventors: John R. Briggs, Midland, MI (US);
Jasson T. Patton, Midland, MI (US);
Sonet Vermaire-Louw, Vlissingen (NL);
Peter M. Margl, Midland, MI (US);
Henk Hagen, Terneuzen (NL);
Daryoosh Beigzadeh, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 309 days.

(21) Appl. No.: 13/002,719

(22) PCT Filed: Jul. 22, 2009

(86) PCT No.: PCT/US2009/051347
§ 371 (c)(1),
(2), (4) Date: Jan. 5, 2011

(87) PCT Pub. No.: WO2010/019360
PCT Pub. Date: Feb. 18, 2010

(65) Prior Publication Data
US 2011/0137086 A1    Jun. 9, 2011

Related U.S. Application Data

(60) Provisional application No. 61/088,186, filed on Aug. 12, 2008.

(51) Int. Cl.
*C07C 41/06* (2006.01)
*C07C 43/178* (2006.01)
*C07C 1/20* (2006.01)
(52) U.S. Cl.
CPC ............... *C07C 41/06* (2013.01); *C07C 43/178* (2013.01); *C07C 1/20* (2013.01)
USPC .......................................... 568/690; 585/639
(58) Field of Classification Search
CPC .......... C07C 41/06; C07C 43/178; C07C 1/20
USPC .......................................... 568/690; 585/639
See application file for complete search history.

(56) References Cited

U.S. PATENT DOCUMENTS

| | | | |
|---|---|---|---|
| 5,254,782 A | 10/1993 | Schaart et al. | |
| 6,051,738 A | 4/2000 | Traenckner et al. | |
| 6,147,238 A | 11/2000 | Traenckner et al. | |
| 6,153,780 A | 11/2000 | Traenckner et al. | |
| 6,160,168 A | 12/2000 | Traenckner et al. | |
| 6,310,259 B1 | 10/2001 | Keim et al. | |
| 7,026,523 B2 | 4/2006 | Rottger et al. | |
| 7,030,286 B2 | 4/2006 | Rottger et al. | |
| 7,115,790 B2 | 10/2006 | Beller et al. | |
| 7,141,539 B2 | 11/2006 | Edwards | |
| 7,368,621 B2 | 5/2008 | Krissmann et al. | |
| 7,425,658 B2 | 9/2008 | Edwards | |

FOREIGN PATENT DOCUMENTS

| WO | WO-92/10450 A1 | 6/1992 |
|---|---|---|
| WO | WO-00/02890 | 1/2000 |

OTHER PUBLICATIONS

Vollmuller et al. (Eur. J. lnorg. Chem., Aug. 2000, Issue 8, pp. 1825-1832).*
Basato et al Journal of mollecular Catalysis A Chemical 1999 p. 313-16 v145.
Fritz et al Journal of the Chemical Society 1965 p. 5210-16.
Palkovits et al A European Journal 2008 p. 8995-9005 v14.
Palkovits et al Chemsuschem 2008 p. 193-6 v1.
Prinz et al A European Journal 1999 p. 2069-76 v5.
Vuoti et al Journal of organometallic Chemistry 2007 p. 5044-52 v692.
Wada et al Journal of Chemical Research 1985 p. 38-39.
Maddock et al Journal of Organometallics 2000 p. 2684-2689 v19.
Liu et al Journal of Organometallic Chemistry 2007 p. 210-216 v26.
PCT/US2009/051347 International Search Report, Jan. 2010.
PCT/US2009/051347 Written Opinion.
PCT/US2009/051347 Intl Preliminary Report on Patentability, Aug. 2010.

* cited by examiner

*Primary Examiner* — Rosalynd Keys

(57) ABSTRACT

In an improved process for telomerizing butadiene, contact butadiene and an organic hydroxy compound represented by formula ROH (I), wherein R is a substituted or unsubstituted $C_1$-$C_{20}$-hydrocarbyl and the organic hydroxy compound is not glycerol, in a reaction fluid in the presence of a palladium catalyst and a phosphine ligand represented by formula $PAr_3$ (II), wherein each Ar is independently a substituted or unsubstituted aryl having a hydrogen atom on at least one ortho position, at least two Ar groups are ortho-hydrocarbyloxyl substituted aryls. The phosphine ligand has a total of two (2), three (3), four (4), five (5), or six (6) substituted or unsubstituted $C_1$-$C_{20}$-hydrocarbyloxyls, and optionally, any two adjacent substituents on an Ar group can be bonded to form a 5- to 7-membered ring.

10 Claims, No Drawings

PROCESS FOR TELOMERIZATION OF BUTADIENE

This application is a non-provisional application claiming priority from the U.S. Provisional Patent Application No. 61/088,186, filed on Aug. 12, 2008, entitled "AN IMPROVED PROCESS FOR TELOMERIZATION OF BUTADIENE," the teachings of which are incorporated by reference herein, as if reproduced in full hereinbelow.

The present invention relates generally to a process for telomerizing 1,3-butadiene in the presence of an organic hydroxy compound, a palladium catalyst and a phosphine ligand.

Telomerization of 1,3-butadiene, hereinafter simply referred to as butadiene, in the presence of a nucleophile, such as an alkanol, is a known reaction for oligomerizing, especially dimerizing, butadiene to produce commercially useful chemicals having eight or more carbon atoms. The reaction typically produces a mixture comprising primarily a linear product, 1-alkoxy-2,7-octadiene, and minor products such as a branched 3-alkoxy-1,7-octadiene and 1,3,7-octatriene. The linear product is a useful starting material for producing 1-octene, a co-monomer for producing plastics. See for example WO92/10450 (Bohley et al.), U.S. Patent Application Publication 2005/0038305 (Edwards) and U.S. Pat. No. 7,030,286 (Rottger et al.).

In producing 1-octene from a butadiene telomerization product mixture, the branched product 3-alkoxy-1,7-octadiene leads to production of undesirable by-products, 2- and 3-octenes, which may need to be removed from the desired product 1-octene. Therefore, it is desirable to maximize a 1-alkoxy-2,7-octadiene to 3-alkoxy-1,7-octadiene molar ratio in the butadiene telomerization product mixture when 1-octene is a preferred final product with little or no, preferably no, 2-octene or 3-octene.

The telomerization reaction is generally catalyzed by a ligand complex of a transition metal selected from a group consisting of iron (Fe), cobalt (Co), nickel (Ni), ruthenium (Ru), rhodium (Rh), palladium (Pd), osmium (Os), iridium (Ir) and platinum (Pt). Preferably, the transition metal is palladium. Phosphines are examples of ligands that can form efficient palladium catalysts suitable for use in producing 1-alkoxy-2,7-octadiene.

U.S. Pat. No. 7,141,539 and U.S. 2005/0038305, both of Edwards, relate generally to using palladium complexes of certain alkoxy substituted phosphines (e.g., tris-(2,4,6-trimethoxyphenyl)phosphine and tris-(4-methoxyphenyl)phosphine) as catalysts to promote butadiene telomerization with an alkanol or an α,ω-diol to form a product comprising primarily 1-alkoxy- or 1-hydroxyalkoxy-substituted octadiene, respectively.

SUMMARY OF THE INVENTION

In some embodiments, this invention provides an improved process for telomerizing butadiene, the process comprising contacting butadiene and an organic hydroxy compound represented by formula ROH (I), wherein R is a substituted or unsubstituted $C_1$-$C_{20}$-hydrocarbyl and the organic hydroxy compound is not glycerol, in a reaction fluid in the presence of a palladium catalyst and a phosphine ligand, the improvement comprising, a) the phosphine ligand being selected from a group represented by formula (II):

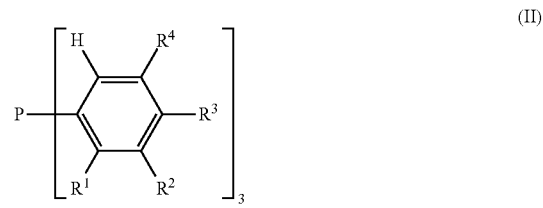

wherein:

$R^1$, $R^2$, $R^3$ and $R^4$ are each independently selected from a group consisting of hydrogen, halogen, substituted and unsubstituted $C_1$-$C_{20}$-hydrocarbyls, and substituted and unsubstituted $C_1$-$C_{20}$-hydrocarbyloxyls, provided that at least two $R^1$ moieties are independently selected from substituted or unsubstituted $C_1$-$C_{20}$-hydrocarbyloxyls and that the phosphine ligand has a total of two (2), three (3), four (4), five (5), or six (6) substituted or unsubstituted $C_1$-$C_{20}$-hydrocarbyloxyls;

wherein optionally on each phenyl ring, $R^1$ is bonded to $R^2$ to form a 5- to 7-membered ring, $R^2$ is bonded to $R^3$ to form a 5- to 7-membered ring, or $R^3$ is bonded to $R^4$ to form a 5- to 7-membered ring; and b) which contacting occurs in a reaction fluid that comprises the butadiene, the organic hydroxy compound, the palladium catalyst and the phosphine ligand under conditions and for a reaction time sufficient to yield a product mixture comprising a linear product 1-RO-2,7-octadiene and a branched product 3-RO-1,7-octadiene with a linear product to branched product molar ratio of greater than (>) 25/1 and a catalyst efficiency at least (≥) 150 grams (g) of the linear product per g palladium per hour (g/g/hr), wherein R is as defined above.

All percentages, preferred amounts or measurements, ranges and endpoints thereof herein are inclusive, that is, "a range from 5 to 10" includes 5 and 10.

A "hydrocarbyl" is a univalent moiety derived from a hydrocarbon by removal of one hydrogen atom from one carbon atom, which carbon atom is also defined as an "alpha" carbon or a carbon placed in the alpha position. A hydrocarbyl can be an alkyl, alkenyl, alkynyl, or aryl, a univalent moiety derived from an alkane, alkene, alkyne, or arene, respectively, by removal of one hydrogen atom from one carbon atom.

A "hydrocarbylene" is a divalent moiety derived from a hydrocarbon by removal of two hydrogen atoms from two carbon atoms. A hydrocarbylene, except methylene, has two alpha carbon atoms, each named according to its position in the hydrocarbylene.

A "beta" carbon/position is a carbon atom that is directly bonded to the alpha carbon. A gamma carbon/position is a carbon atom that is directly bonded to a beta carbon and is two bonds away from the alpha carbon.

A "substituted hydrocarbyl" or "substituted hydrocarbylene" means that one or more hydrogen (H) or carbon (C) atom(s) in the hydrocarbyl or the hydrocarbylene is substituted by one or more heteroatom(s) or one or more functional group(s) that contain one or more heteroatom(s) such as nitrogen, oxygen, sulfur, phosphorus, boron, fluorine, chlorine, bromine, and iodine.

A "hydrocarbyloxyl" or "substituted hydrocarbyloxyl" is a univalent moiety having a generic formula of RO—, wherein R is a hydrocarbyl or substituted hydrocarbyl, respectively, as defined above. A hydrocarbyloxyl is an alkoxyl when R is an alkyl, or an aryloxyl when R is an aryl.

The "$pK_b$" of a base has its ordinary definition of being equal to "$-\log_{10}K_b$", where $K_b$ is the dissociation constant of the acid conjugate to the base in water.

Define number of carbon atoms or a range thereof forming a moiety or compound by prefixing the moiety or compound with a formula "$C_m$—" or "$C_m$—$C_n$—," respectively, wherein m and n are integers.

Abbreviations and symbols "° C.," "g," "L," "ml," "mol," "mmol," "M," "mM," "conv," "eq," "psi," "mPa" and "NMR" are used, respectively, for "degree Celsius," "gram," "liter," "milliliter," "mole," "millimole," "moles/liter," "millimole/liter," "conversion," "equivalent," "pounds per square inch," "mega Pascal" and "nuclear magnetic resonance," respectively, and plural forms thereof.

In some embodiments, this invention provides a process that comprises contacting butadiene with an organic hydroxy compound of formula ROH (I) in the presence of a palladium catalyst and a phosphine ligand represented by formula (II):

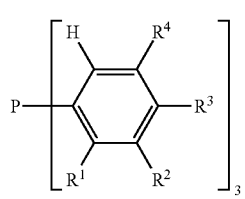

wherein the organic hydroxy compound and $R^1$ through $R^4$ are as defined above.

Contacting occurs in a reaction fluid that comprises the butadiene, the organic hydroxy compound, the palladium catalyst, and the phosphine ligand. The reaction fluid may further comprise one or more optional component(s), such as an organic solvent, a catalyst promoter, a catalyst stabilizer, or a butadiene polymerization inhibitor, which optional components will be described in more detail hereinbelow.

The above phosphine ligand advantageously has ≥two aryls each of which is substituted by one $C_1$-$C_{20}$-hydrocarbyloxyl substituent on only one of its ortho positions.

Examples of suitable phosphines include, but are not limited to, tris-(2-methoxyphenyl)phosphine, tris-(2-ethoxyphenyl)phosphine, tris-(2-propoxyphenyl)phosphine, tris-(2-i-propoxyphenyl)phosphine, tris-(2-butoxyphenyl)phosphine, tris-(2-sec-butoxyphenyl)phosphine, tris-(2-t-butoxyphenyl)phosphine, tris-(2-phenoxyphenyl)phosphine, tris-(2-p-methylphenoxyphenyl)phosphine, tris-(2-p-trifluoromethylphenoxyphenyl)phosphine, tris-(2-trifluoromethoxyphenyl)phosphine, tris-(2-methoxy-4-fluorophenyl)phosphine, tris-(2-methoxy-4-chlorophenyl) phosphine, tris-(2-methoxy-4-methylphenyl)phosphine, tris-(2,4-dimethoxyphenyl)phosphine, tris-(2,3-dihydrobenzofuran-7-yl)phosphine, trichroman-8-ylphosphine, tris-(2,3,4,5-tetrahydrobenzo[b]oxepin-9-yl) phosphine, tris-(2,3-dihydrobenzo[b][1,4]dioxin-5-yl) phosphine bis-(2-methoxyphenyl)phenylphosphine, bis-(2,4-dimethoxyphenyl)phenylphosphine, bis-(2-ethoxyphenyl) phenylphosphine, bis-(2-propoxyphenyl)phenylphosphine, bis-(2-i-propoxyphenyl)phenylphosphine, bis-(2-butoxyphenyl)phenylphosphine, bis-(2-sec-butoxyphenyl)phenylphosphine, bis-(2-t-butoxyphenyl)phenylphosphine, bis-(2-phenoxyphenyl)phenylphosphine, bis-(2-p-methylphenoxyphenyl)phenylphosphine, bis-(2-p-trifluoromethylphenoxyphenyl)phenylphosphine, bis-(2-trifluoromethoxyphenyl)phenylphosphine, bis-(2-methoxy-4-fluorophenyl)phenylphosphine, bis-(2-methoxy-4-chlorophenyl)phenylphosphine, bis-(2-methoxy-4-methylphenyl)phenylphosphine, bis-(2,3-dihydrobenzofuran-7-yl)phenylphosphine, bis-(2-methoxyphenyl)(4-(trifluoromethyl)phenyl)phosphine, bis-(2,3-dihydrobenzo-[][1,4]dioxin-5-yl)phenylphosphine, dichroman-8-ylphenylphosphine, and bis-(2,3,4,5-tetrahydrobenzo[b]oxepin-9-yl)phenylphosphine.

Preferred suitable phosphines include, but are not limited to, tris-(2-methoxyphenyl)phosphine, tris-(2,4-dimethoxyphenyl)phosphine, bis-(2-methoxyphenyl)phenylphosphine, tris-(2-methoxy-4-fluorophenyl)phosphine, and tris-(2-methoxy-4-chlorophenyl)phosphine. More preferred suitable phosphines include, but are not limited to, tris-(2-methoxyphenyl)phosphine, bis-(2-methoxyphenyl)phenylphosphine, tris-(2-methoxy-4-fluorophenyl)phosphine, and tris-(2-methoxy-4-chlorophenyl)phosphine.

The process employs the phosphine ligand in an amount sufficient to stabilize the palladium catalyst in the reaction fluid and provide a catalyst efficiency sufficient to produce a product mixture comprising a linear product 1-RO-2,7-octadiene and a branched product 3-RO-1,7-octadiene with a molar ratio of the linear product to the branched product (L/B ratio) ≥25/1, preferably ≥26/1. The amount of phosphine ligand provides an initial ligand to palladium molar ratio ≥1.0. The initial phosphine ligand to palladium ratio is preferably ≥1.5 to substantially stabilize the palladium catalyst in the reaction fluid. The phosphine ligand may at least partially decompose during the course of the telomerization reaction. Preferably maintain a phosphine ligand to palladium ratio of ≥1.0 throughout the course of the telomerization reaction, either by adding >one molar equivalent of the phosphine ligand, or alternatively, by adding additional amount of the phosphine ligand throughout the telomerization reaction. The initial phosphine ligand to palladium ratio is advantageously less than (<) 50, and preferably <40, so that the phosphine ligand provides sufficient stabilization to the palladium catalyst, as well as catalyst efficiency sufficient to produce the product mixture. Measure catalyst efficiency by an average production rate of g of the linear product (LP) per g palladium (Pd) per hour (hr) or gLP/gPd/hr. The catalyst efficiency is preferably ≥150 gLP/gPd/hr, more preferably ≥200 gLP/gPd/hr, still more preferably ≥400 gLP/gPd/hr, and still more preferably ≥1000 gLP/gPd/hr.

Using a preferred phosphine ligand, the process produces a telomerization product mixture comprising the linear (L) product 1-RO-2,7-octadiene and the branched (B) product 3-RO-1,7-octadiene preferably with a catalyst efficiency ≥150 gLP/gPd/hr and a L/B ratio at least 25/1.

The organic hydroxy compound can have one or more hydroxyl groups, except that the organic hydroxy compound is not glycerol. Examples of suitable organic hydroxy compounds methanol, ethanol, 1-propanol, 2-propanol, 1-butanol, 2-butanol, t-butanol, 2-methylpropan-1-ol, 2,2-dimethylpropan-1-ol, pentanols, hexanols, heptanols, octanols, decanols, dodecanols, tetradecanols, hexadecanols, octadecanols, phenol, ethylene glycol, propylene glycol, sorbitol, glucose, fructose, sucrose, and mixtures thereof.

The process optionally comprises additional steps to produce 1-octene from the telomerization product mixture. A typical process of converting the telomerization product mixture to 1-octene involves first subjecting the telomerization product mixture under hydrogenation condition to reduce 1-RO-2,7-octadiene to 1-RO-octane, which can also be written as RO-1-octyl ether. Then either thermally or catalytically decompose the ether to eliminate the RO— moiety and a beta hydrogen atom of the 1-octyl moiety to regenerate the organic hydroxy compound ROH and produce 1-octene. Advantageously, separate and reuse the organic hydroxy compound ROH in the butadiene telomerization reaction. WO92/10450 (Bohley et al.), U.S. 2005/0038305 (Edwards), U.S. Pat. No. 7,030,286 (Winger et al.), and U.S. Pat. No. 7,368,621 (Krissmann et al.) exemplify such 1-octene producing processes.

The present invention stems from a surprising discovery that catalyst efficiency is inversely correlated to the molar concentration of the organic hydroxy compound, preferably methanol, when using a phosphine ligand as disclosed above.

The process employs the organic hydroxy compound in an amount such that a maximum concentration of the organic hydroxy compound in the reaction fluid during the course of the telomerization reaction is advantageously less than (<) 6.0 moles per liter (M), preferably <5.0 M, and still more preferably <3.5 M, of the reaction fluid, and is advantageously >1.0 M, preferably >2.5 M, of the reaction fluid.

One can feed the organic hydroxy compound into the reaction fluid or zone batch-wise, continuously or a combination thereof. One preferably feeds each batch of organic hydroxy compound in an amount such that the organic hydroxy compound has an initial concentration of >1.0 M of reaction fluid, and a maximum concentration of <6.0 M of reaction fluid at any time of the reaction.

When employing continuous feeding, feed the organic hydroxy compound into the reaction fluid in a feed rate such that the concentration of the organic hydroxy compound is substantially maintained within the ranges described hereinabove for a percentage of the reaction time. The percentage is advantageously >30%, preferably >40%, and more preferably >50%, and is advantageously <100%, preferably <90%, and more preferably <80% of the reaction time.

As a starting material, butadiene can be employed as pure butadiene or as a butadiene-containing $C_4$-hydrocarbon mixture. Other $C_4$-hydrocarbons in such a $C_4$-hydrocarbon mixture include butenes and butanes. The other $C_4$-hydrocarbons do not substantially influence conversion of the butadiene present in the $C_4$-hydrocarbon mixture or selectivity towards the desired telomerization product. When the $C_4$-hydrocarbon mixture contains acetylenes, optionally remove the acetylenes by, for example, selectively hydrogenating the $C_4$-hydrocarbon mixture before use because acetylenes may decrease palladium catalyst efficiency.

The process can employ any palladium catalyst or catalyst precursor known in the art. The process advantageously employs palladium (Pd) metal, a Pd(II) compound, a Pd(0) complex, or a mixture thereof as the catalyst or as a catalyst precursor that forms the catalyst under the reaction conditions in the process. Examples of suitable forms of Pd metal include Pd powder, Pd black and Pd on carbon. Examples of suitable Pd(II) compounds include Pd(II) chloride, Pd(II) bromide, Pd(II) acetate, Pd(II) formate, Pd(II) propionate, Pd(II) borate, Pd(II) citrate, Pd(II) hydroxide, Pd(II) octanoate, Pd(II) carbonate, Pd(II) sulfate, Pd(II) nitrate, Pd(II) acetylacetonate, Pd(II) alkyl-sulfonate, disodium palladium tetrachloride ($Na_2PdCl_4$), dipotassium palladium tetrachloride ($K_2PdCl_4$), dichlorobis(benzonitrile)palladium, allylpalladium chloride, allylpalladium acetate, triallylpalladium, and 1,5-cyclooctadienepalladium(II) chloride. When using Pd halides, an activator needs to be added to the reaction. Preferred Pd(II) salts have organic anions, for example, Pd acetate or Pd acetylacetonate. Examples of ligands in suitable palladium(0) complexes include heteroatom-containing compounds, alkynes, alkenes and dienes. Examples of heteroatom-containing compounds are phosphines, phosphites, phosphonites, phosphinites, amines, nitrites and pyridines. Specific examples are bis(dibenzylideneacetone)palladium(0), tris(dibenzylideneacetone)dipalladium(0) and bis(1,5-cyclooctadiene)palladium. Preferably, the Pd catalyst or precursor is a divalent Pd compound, for example, Pd(II) acetylacetonate.

The process employs a Pd catalyst concentration in the reaction fluid sufficient to produce a telomerization product mixture comprising 1-RO-2,7-octadiene. Pd catalyst concentration depends on a particular phosphine ligand employed and other reaction conditions, such as butadiene feed, either in pure form or in a $C_4$-hydrocarbon mixture. Calculate Pd catalyst concentration in parts per million by weight (ppmw) of Pd based on the weight of the reaction fluid. The concentration is advantageously >one (1) ppmw, preferably >two (2) ppmw, and more preferably >three (3) ppmw of Pd, and is advantageously <100 ppmw, preferably <75 ppmw, and more preferably <50 ppmw of Pd.

Pd catalyst can be introduced as an active catalyst with the phosphine ligand into the reaction fluid or a reaction zone. Advantageously, introduce a catalyst precursor, either separately or together with the phosphine ligand, into the reaction fluid to produce the active catalyst with the phosphine ligand under the reaction conditions.

When a Pd(II) compound is used as the catalyst precursor, it generally takes a certain period of time to form the active catalyst under the reaction conditions. This time period, which depends on electronic and steric properties of the phosphine ligand, is referred to as an induction period. The induction period is generally >one (1) minute, but <two (2) hours. Optionally employ a catalyst promoter to shorten or essentially eliminate the induction period. Select a catalyst promoter from compounds having a $pK_b$ >five (5), preferably >six (6), more preferably >seven (7), and still more preferably >eight (8). Preferably, select a catalyst promoter from a group consisting of tertiary amines, alkali metal borohydrides, oxides, and compounds having a generic formula $(R^5O^-)_n M^{n+}$, wherein $R^5$ is hydrogen, a $C_1$-$C_{20}$-hydrocarbyl, or a substituted $C_1$-$C_{20}$-hydrocarbyl, M is an alkali metal, alkaline earth metal or quaternary ammonium, and n is one (1) or two (2).

The catalyst promoter, when used, is present in an amount that provides a molar ratio of catalyst promoter to Pd in the reaction fluid of ≥0.01, preferably ≥0.1, more preferably ≥0.5 up to <1000, preferably <800, and more preferably <600.

The process optionally employs an organic solvent to carry out the telomerization reaction. The process can employ any organic solvent so long as the solvent does not substantially interfere with the process, e.g. a solvent selected from a group consisting of $C_4$-$C_{12}$ alkanes, $C_4$-$C_{12}$ alkenes, $C_6$-$C_{12}$ arenes, $C_4$-$C_{12}$ ethers, $C_5$-$C_{12}$ tertiary amines, and mixtures thereof.

The organic solvent, when present, is employed in an amount such that the solvent comprises ≥20 wt %, preferably ≥30 wt %, and <80 wt %, preferably <70 wt % of the reaction fluid by weight, each wt % being based on reaction fluid weight.

Optionally, the process employs a carboxylic acid to stabilize the Pd catalyst in solution, particularly during storage. Examples of such carboxylic acids include formic acid, acetic acid, propionic acid, butyric acid, valeric acid, caproic acid, enanthic acid, caprylic acid, pelargonic acid, capric acid, lauric acid, palmitic acid, stearic acid, benzoic acid, and benzilic acid. The process preferably employs a catalyst stabilizer in an amount sufficient to stabilize the Pd catalyst. The amount provides preferably a molar ratio of the stabilizer to Pd ≥0.5, more preferably ≥one (1), and preferably <four (4), more preferably <two (2).

Optionally, the process employs a radical inhibitor to prevent butadiene polymerization. Any known radical inhibitor is suitable so long as it does not substantially interfere with the telomerization reaction. Examples of suitable radical inhibitors include diethylhydroxyamine (DEHA), 2,6-di-tert-butyl-4-methylphenol (BHT), 4-tert-butylcatechol, hydroquinone, catechol, and phenol. When used, the radical inhibitor is present in an amount sufficient to provide a concentration of the radical inhibitor ≥one (1) ppmw, more preferably ≥five (5) ppmw, and preferably <100 ppmw, more preferably <50 ppmw, based on the weight of the reaction fluid.

The Pd catalyst/precursor, phosphine ligand, catalyst stabilizer, catalyst promoter, and radical inhibitor, also referred to as "catalyst components", can each be fed into the reaction fluid or zone separately or together as a mixture of >two catalyst components. Each catalyst component can be fed into the reaction fluid or zone either in its original form, or as a solution or as a slurry in the organic hydroxy compound, a solvent if employed, or a mixture thereof.

The process optionally includes preparation of a catalyst or catalyst precursor stock solution by dissolving a Pd compound/complex mentioned hereinabove, the phosphine ligand, and a catalyst stabilizer in the organic hydroxy compound, in an organic solvent if employed, or in a mixture of the organic hydroxy compound and an organic solvent. The phosphine ligand, the catalyst stabilizer, or both can react with the Pd compound to form one or more new Pd compounds/complexes comprising the phosphine ligand, the catalyst stabilizer, or both in the stock solution.

The process can be carried out either in batch or continuously. Any batch or continuous reactor can be employed. Examples of suitable reactors include stirred tank reactors, tubular reactors, and combinations thereof.

The telomerization reaction is advantageously conducted under an inert atmosphere, such as nitrogen, argon, or helium, and at a reaction temperature sufficient to produce the linear product 1-RO-2,7-octadiene at a catalyst efficiency within the ranges described hereinabove. The reaction temperature is preferably >40° C., more preferably >50° C., and still more preferably >60° C., and is preferably <120° C., more preferably <110° C., and still more preferably <100° C. For a given catalyst, catalyst efficiency increases with increasing temperature within the ranges stated above.

The telomerization reaction is advantageously conducted in a sealed reactor at a pressure at least equal to the sum of vapor pressures of reaction fluid components, such as butadiene, the organic hydroxy compound and the organic solvent if present, at a reaction temperature within the ranges described hereinabove. The pressure can be increased above the sum of the vapor pressures by pressurizing an inert gas, such as nitrogen, into the reactor. The pressure is preferably >0.1 mega Pascal (mPa) (15 pounds per square inch (psi)), more preferably >0.2 mPa (29 psi), and still more preferably >0.4 mPa (58 psi), and is preferably <four (4) mPa (584 psi), more preferably <three (3) mPa (438 psi), and still more preferably <two (2) mPa (292 psi).

The telomerization reaction is conducted for a reaction time sufficiently long to achieve a butadiene conversion of ≥50%, preferably ≥70%, and more preferably ≥90%, when pure butadiene is employed; or a butadiene conversion of advantageously ≥90%, preferably ≥95%, and more preferably ≥98%, when a butadiene-containing $C_4$-hydrocarbon mixture is employed. The reaction time is preferably >one (1) minute, more preferably >five (5) minutes, and still more preferably >10 minutes, and is preferably <24 hours, more preferably <18 hours, and still more preferably <12 hours.

Depending on physical properties of the organic hydroxy compound, palladium catalyst, phosphine ligand, and optional solvent, one can isolate the desired product, e.g., 1-RO-2,7-octadiene or a mixture thereof with 3-RO-1,7-octadiene, by subjecting the reaction mixture to one or more distillation, extraction, or other well known separation techniques, or a combination thereof, to separate unconverted reactants and the optional solvent.

Telomerization products obtained via the above process find use as intermediates for a variety of applications, for example, in producing surfactants, herbicides, saturated ethers, alcohols, acids, esters and olefins.

Solvent Preparation

Prepare anhydrous methylcyclohexane (MCH), tetrahydrofuran (THF) and methanol ($CH_3OH$) purchased from Aldrich by flowing each solvent through a short column of activated alumina and a layer of silica gel to keep alumina fines from coming through the column in a glovebox under nitrogen. Treat dibutyl ether, purchased from Aldrich and used as an internal standard for gas chromatography (GC) analysis, by first stirring it over sodium (Na)/potassium (K) alloy overnight and then flowing it through a short column of activated alumina and a layer of silica gel in a glovebox under nitrogen.

Tris-(2,4-dimethoxyphenyl)phosphine (L2) preparation

Prepare a mixture by adding dropwise a THF (10 mL) solution of phosphorus trichloride ($PCl_3$, 1.03 g, 7.50 mmol) into a stirring THF solution of 2,4-dimethoxyphenylmagnesium bromide (50.0 mL of 0.5 M solution in THF, 25.0 mmol) at −78° C. Stir the mixture at −78° C. for 30 minutes, at room temperature for three (3) hours, and then at 50° C. overnight. Remove volatiles from the mixture to obtain a yellow residue, which is dissolved in acetonitrile and filtered to obtain a first filtrate. Remove volatiles from the first filtrate under vacuum to obtain a pale yellow solid. Add acetonitrile dropwise to the pale yellow solid with agitation until essentially all the solid dissolves to obtain a solution. Filter the solution to remove any residual solid to obtain a second filtrate. Place the second filtrate in a freezer (−10° C.) overnight to obtain a white crystalline solid. Isolate the crystalline solid by decanting off the liquor and drying the crystalline solid under vacuum (1.07 g, 32.3%). $^1$H NMR ($CD_3CN$): δ 3.75 (s, 3H), 3.84 (s, 3H), 6.45-6.65 (m, 3H). $^{31}$P NMR ($CD_3CN$): δ −42.1.

Tris-(2-methoxy-4-fluorophenyl)phosphine (L4) preparation

Charge magnesium (Mg) turnings (1.18 g, 48.8 mmol) and five (5) mL THF under nitrogen into a 3-neck round-bottom flask equipped with a reflux condenser and heat the flask contents to 50° C. with a heating mantle. Add dropwise a solution of 2-bromo-5-fluoroanisol (5.00 g, 24.39 mmol) and 1,2-dibromoethane (0.51 g, 2.7 mmol) in THF (total volume of 15 mL) with stirring. Remove the heating mantle five (5) minutes after commencing the addition as the reaction heat becomes sufficient to maintain the reaction temperature. After completing the addition in about 50 minutes to yield a first mixture, reflux the first mixture for an additional 30 minutes to yield a brown solution. After allowing the brown solution to cool to room temperature, separate the brown solution from the unreacted Mg turnings by transferring the brown solution via a cannula into a 100 mL round-bottom flask under nitrogen. Cool the brown solution to −70° C. and add dropwise a solution of $PCl_3$ (1.038 g, 7.56 mmol) in seven (7) mL THF with stirring over a period of 30 minutes to yield a second mixture. Heat the second mixture to 50° C. and stir the second mixture for two (2) hours at 50° C. After cooling flask contents to room temperature and transferring the flask into a glovebox, filter the second mixture and wash the filter with diethyl ether (20 mL) to obtain a filtrate. Remove volatiles from the filtrate under vacuum to yield a light brown solid. Dissolve this light brown solid in benzene under an inert nitrogen atmosphere to obtain a benzene solution and wash the benzene solution with deionized water (3×20 mL). Dry the organic layer over $MgSO_4$ and then filter it to obtain a dry benzene solution. Remove benzene under vacuum to isolate an off-white solid, which is further purified by recrystallization from acetonitrile (1.60 g, 52.1% yield). $^1$H NMR ($C_6D_6$): δ 2.99 (s, 3H), 6.30-6.33 (m, 1H), 6.49-6.52 (t of d, $^3J_{HH}$=8.2, 2.3, 1H), 6.82-6.86 (m, 1H). $^{31}$P NMR ($C_6D_6$, externally referenced using $H_3PO_4$): δ −38.9. $^{19}$F NMR (C6D6): −110.8 to −110.90 (m, 1F).

Tris-(2-methoxy-4-chlorophenyl)phosphine (L5) preparation

Replicate the procedure above for preparation of L4 with the following exceptions: a) Mg turnings (0.604 g, 24.8 mmol) and two (2) mL THF; b) dropwise add a solution of 2-bromo-5-chloroanisol (5.0 g, 22.6 mmol) and 1,2-dibromoethane (0.31 g, 1.65 mmol) in THF (total volume of 13 mL) to yield a first mixture; c) reflux the first mixture an additional 4 hours, instead of 30 minutes; d) dropwise add a solution of $PCl_3$ (0.961 g, 7.00 mmol) in THF (6 mL) to yield a second mixture; e) Reflux the second mixture for 3.5 hours, instead of heating at 50° C. for two (2) hours; and e) Isolate the product as a crystalline light brown solid (1.60 g, 50.2% yield). $^1$H NMR ($C_6D_6$): δ 2.97 (s, 3H), 6.60-6.63 (dd, $^3J_{HH}$=4.3 Hz, 1.7 Hz, 1H), 6.74-6.82 (m, 2H). $^{31}$P NMR ($C_6D_6$, externally referenced using $H_3PO_4$): δ −37.6.

Preparation of Bis(2-methoxyphenyl)(4-(trifluoromethyl)phenyl)phosphine (L6)

Stir 1-Bromo-4-(trifluoromethyl)benzene (0.593 g, 2.63 mmol) in diethylether (30 mL) while dropwise adding 0° C. as n-BuLi (2.63 mmol, 1.32 mL of 2.0 M solution in cyclohexane). Allow this mixture to stir for an additional hour, then add chlorobis(2-methoxyphenyl)phosphine (0.739 g, 2.63 mmol) as a solid. Continue stirring for four hours at room temperature, then remove volatiles were removed and dissolve residue benzene and filter to remove salts to yield a yellow residue. Dissolve the residue in a minimum amount of acetonitrile, filter the solution, and place the solution in a glovebox freezer (−10° C.) to precipitate crystals out of solution. Isolate the crystals by decanting off the liquid and drying under vacuum. Replicate crystallization and crystal isolation two more times to yield a white microcrystalline solid (0.419 g, 49.3%). $^1$H NMR ($C_6D_6$): δ 3.16 (s, 6H), 6.47-6.52 (m, 2H), 6.71-6.77 (m, 2H), 6.90-6.95 (m, 2H), 7.08-7.15 (m, 2H), 7.21-7.25 (m, 2H), 7.31-7.37 (m, 2H). $^{13}$C NMR ($C_6D_6$): 55.2, 110.6, 121.4, 125.1 (m), 130.7, 134.23, 134.25, 134.4, 134.7, 143.4, 161.8 (d, 15.7 Hz). $^{31}$P NMR ($C_6D_6$, externally referenced using $H_3PO_4$): δ −24.6. $^{19}$F NMR ($C_6D_6$, externally referenced using $CCl_3F$): −62.7.

TABLE 1

Ligands employed to illustrate some embodiments of the invention

| No. | Name | Source | Comments |
|---|---|---|---|
| L1 | Tris-(2-methoxyphenyl)-phosphine | Strem | Having 3 ortho-methoxy substituted phenyl rings. |
| L2 | Tris-(2,4-dimethoxyphenyl)-phosphine | Prepared | Having 3 ortho- and para-methoxy substituted phenyl rings. |
| L3 | Bis-(2-methoxyphenyl)phenyl-phosphine | Strem | Having 2 ortho-methoxy substituted phenyl rings. |
| L4 | Tris-(2-methoxy-4-fluorophenyl)-phosphine | Prepared | Having 3 ortho-methoxy and para-fluoro substituted phenyl rings. |
| L5 | Tris-(2-methoxy-4-chlorophenyl)-phosphine | Prepared | Having 3 ortho-methoxy and para-chloro substituted phenyl rings |
| L6 | Bis(2-methoxyphenyl)(4-(trifluoro-methyl)phenyl)phosphine | Prepared | Having 2 ortho-methoxy substituted phenyl rings and a para-trifluoromethyl substituted phenyl ring. |

Catalyst Stock Solution Preparation

Prepare a catalyst stock solution using L1 according to the following procedure:

Dissolve Pd(II) acetylacetonate ($Pd(acac)_2$, 0.0294 g, 0.097 mmoles, Aldrich: 05615EH), L1 (0.0642 g, 0.193 mmoles) and acetic acid (AcOH, 0.097 mmoles, 0.50 mL of 0.193 M AcOH in $CH_3OH$) in MeOH to obtain a solution having a total volume of 50.0 mL. Stir this solution for approximately 30 minutes to obtain a Pd-L1 catalyst stock solution having 1.93 mmol/liter of palladium and 3.86 mmol/liter of L1. Acetic acid is used to stabilize the catalyst stock solution during storage.

Prepare catalyst stock solutions using each of the phosphine ligands: L2-L7 according to the above procedure. Each Pd-L catalyst stock solution has the same concentrations of Pd and the ligand as in the Pd-L1 catalyst stock solution.

Prepare a catalyst stock solution according to the procedure hereinabove using each of the comparative ligands (CL) shown in Table 2. Each Pd-CL catalyst stock solution has the same concentrations of Pd and the ligand as in the Pd-L1 catalyst stock solution.

TABLE 2

Comparative ligands

| No. | Name | Source | Comments |
|---|---|---|---|
| CL1 | Triphenylphosphine | Aldrich | None of the phenyl rings is substituted |
| CL2 | 2-Methoxyphenyldiphenyl-phosphine | Aldrich | Having only one ortho-methoxy substituted phenyl ring. |
| CL3 | Tris-(4-methoxyphenyl)-phosphine | Aldrich | No ortho methoxy group on any of the phenyl rings. |
| CL4 | Tris-(2,4,6-trimethoxyphenyl)-phosphine | Strem | Methoxy groups on all ortho and para positions of all 3 phenyl rings. |

Preparation of Stock Solutions of a Catalyst Promoter (Sodium Methoxide (NaOMe)), a Butadiene Polymerization Inhibitor (diethylhydroxyamine (DEHA)), and $H_2O$ Prepare NaOMe and DEHA stock solutions in methanol using anhydrous sodium methoxide (NaOMe) and DEHA from Aldrich as received, and a $H_2O$ stock solution in methanol using degassed and deionized $H_2O$. Prepare, store and dispense all stock solutions under a nitrogen atmosphere. The concentrations of DEHA, H$_2$O, and NaOMe, in their respective stock solutions in methanol are shown in Table 3.

TABLE 3

Concentrations of the minor component in each stock solution

| Stock solution | DEHA in methanol | H$_2$O in methanol | NaOMe in methanol |
|---|---|---|---|
| Concentration of solute (mM) | 4.47 | 3.83 | 19.3 |

General Procedures for Reactor Loading

In a glovebox, syringe butylether, MeOH, methylcyclohexane, a catalyst stock solution, the DEHA/MeOH stock solution, the H$_2$O/MeOH stock solution and the NaOMe stock solution, in this order, into an open Fisher-Porter brand glass reactor that has a maximum working pressure of 200 psi (1.4 mPa). Adding water to the reaction solutions simulates large scale or commercial operations where solvents and reactants generally contain trace amounts of water.

Close the reactor tightly with a reactor head equipped with a pressure gauge, a 150 psi (1.0 mPa) pressure relief valve, and a valve capped with a septum port. Inject 5.5 mL of 1,3-butadiene, using a gas-tight syringe, into the reactor via the septum with the needle placed just below the surface of the liquid. Determine the injected amount of 1,3-butadiene by weighing the syringe before and after the injection.

EXAMPLES (Ex) 1-4

Load four Fisher-Porter brand glass reactors using the Pd-L1 catalyst stock solution according to the general procedure described above with the volumes of the stock solutions and other components in each reactor/example shown in Table 4.

TABLE 4

Solution and components added into reactors for Examples 1-4.

| Example/Reactor NO. | 1 | 2 | 3 | 4 |
|---|---|---|---|---|
| Dibutyl ether (mL) | 5.0 | 5.0 | 5.0 | 5.0 |
| Make-up MeOH (mL) | 1.0 | 0.0 | 1.7 | 9.5 |
| Make-up MCH (mL) | 12.1 | 11.1 | 9.4 | 1.6 |
| Pd-L1 stock solution (mL) | 1.0 | 1.0 | 1.0 | 1.0 |
| DEHA stock solution (mL) | 0.0 | 1.0 | 1.0 | 1.0 |
| H$_2$O stock solution (mL) | 0.0 | 1.0 | 1.0 | 1.0 |
| NaOMe stock solution (mL) | 0.5 | 0.5 | 0.5 | 0.5 |
| 1,3-Butadiene (mL) | 5.5 | 5.5 | 5.5 | 5.5 |
| 1,3-Butadiene (g) | 3.4 | 3.4 | 3.4 | 3.4 |
| Final Volume (mL) | 25.1 | 25.1 | 25.1 | 25.1 |

Table 5 below shows the initial concentrations of the added components in each Ex/reactor, either in moles/liter (M), or parts per million by weight (ppmw) based on the weight of the solution, molar ratios of Pd/L1 and NaOMe/Pd, and the maximum grams of 1-methoxy-2,7-octadiene that can be theoretically produced based on the amount of butadiene charged into each reactor per gram palladium. The acetic acid or its reaction product with Pd(acac)$_2$ in the catalyst stock solution may reduce the NaOMe/Pd molar ratio by up to one (1).

TABLE 5

The initial concentrations of the added components in Ex 1-4

| Example/Reactor NO. | 1 | 2 | 3 | 4 |
|---|---|---|---|---|
| Dibutyl ether (M) | 1.2 | 1.2 | 1.2 | 1.2 |
| MeOH (M) | 2.5 | 3.4 | 5.1 | 12.7 |
| MCH (M) | 3.8 | 3.5 | 2.9 | 0.5 |
| 1,3-Butadiene (M) | 2.5 | 2.5 | 2.5 | 2.5 |
| Pd (ppmw) | 11 | 11 | 11 | 11 |
| L/Pd (mol/mol) | 2 | 2 | 2 | 2 |
| NaOMe/Pd (mol/mol) | 5 | 5 | 5 | 5 |
| DEHA (ppmw) | 0 | 20 | 20 | 20 |
| H$_2$O (ppmw) | 0 | 4 | 4 | 4 |
| Max. g MOD-1/g Pd | 21750 | 21750 | 21750 | 21750 |

Carry out Ex 1-4 by placing the reactors into oil baths preheated to 90° C. and stirring the reactor contents for two (2) hours. Thereafter, remove the reactors from the oil baths, allow the reactors to cool to room temperature, vent the reactors by opening the pressure relief valves, and then opening the reactors to obtain product solutions.

Ex 5-8

Replicate Ex 1-4, except that the reaction times are four (4) hours.

Ex 9 and 10

Replicate Ex 3 and 4 using the catalyst stock solution prepared using L2.

Ex 10-22

Replicate Ex 3, 4 and 8 using the catalyst stock solutions prepared using L3, L4, L5 and L6.

Sample Analysis and Data Acquisition by Gas Chromatography

Analyze the product solutions on a HP 6890 gas chromatography (GC) using a low thermal mass column (LTM-DB-1701) and the following method:

Column: LTM-DB-1701; Length: 30 m; Diameter: 320 µm; Film thickness: 1.0 µm; Mode: constant flow; Initial column flow: 1.4 mL/min Front inlet: Mode: split; Initial Temp: 250° C.; Pressure: 7.19 psi; Split ratio: 50:1; carrier gas: H$_2$.

Detector: Flame ionization detector (FID); Temp: 300° C.; H$_2$ flow: 40.0 mL/min; Air flow: 450.0 mL/min Make up gas: Nitrogen.

Ovens: HP 6890 oven:
  Isothermal at 250° C.
LTM column oven:
  Initial Temp: 65° C. and hold for 110 seconds;
  Ramp at 300° C./min to 120° C. and hold for 100 seconds;
  Ramp at 300° C./min to 250° C. and hold for 233 seconds.
  Total run time: 8.0 minutes.
  Column cooling time to 65° C.: less than 2 minutes.

Prepare a standard sample by using known amounts (grams) of eight (8) GC observable components, methanol, butadiene, dibutyl ether (GC Internal Standard (IS)), 1-methoxy-2,7-octadiene (MOD-1), 3-methoxy-1,7-octadiene (MOD-3), octatrienes, octadienes and vinylcyclohexene. Run the standard sample on the GC to determine retention times and response factors of the eight (8) components. Calculate a response factor (RF(i)) for each component/peak (i) by the equation:

$$RF(i) = [(peak(i)\text{-grams})/(peak(i)\text{-area})]/[(IS\text{-grams}/IS\text{-area})]$$

wherein i=1 through 8.

Prepare a GC sample by taking a one (1) milliliter of a product solution without any dilution. Obtain a chromatogram from the sample using the GC method described above. Use the peak area table of the chromatogram, the RFs of the components (peaks) and the amount of dibutyl ether in the product solution to carry out the following calculations:

Grams of component($i$)=(RF($i$)*peak-area($i$))/($IS$-grams/$IS$-area);

Moles of the component($i$)=(Grams of the component ($i$))/(molecular weight of the component($i$));

Moles of all product=Sum of moles of MOD-1, MOD-3, octatrienes, octadienes and vinylcyclohexene.

Conv(mol %)=(moles of butadiene converted)/(moles of butadiene fed into the reactor);

MOD-1(mol %)=(moles of MOD-1)/(Moles of all products);

MOD-3(mol %)=(moles of MOD-3)/(Moles of all products);

MOD-1/MOD-3 molar($L/B$) ratio=(moles of MOD-1)/(moles of MOD-3);

Catalyst efficiency=(grams of MOD-1)/(grams of Pd)/(hours of reaction time).

Table 6 hereinbelow shows the results from Ex 1-22 calculated according to the above equations.

TABLE 6

Results from examples 1-28

| Ex No. | Ligand No. | [MeOH] (M) | RXT (far) | Conv (mol %) | MOD-1 (mol %) | MOD-3 (mol %) | L/B ratio | Catalyst efficiency[1] |
|---|---|---|---|---|---|---|---|---|
| 1 | L1 | 2.5 | 2 | 33.4 | 94.4 | 3.5 | 27 | 3477 |
| 2 | L1 | 3.5 | 2 | 28.3 | 94.0 | 3.4 | 28 | 2943 |
| 3 | L1 | 5.1 | 2 | 30.3 | 94.2 | 3.3 | 29 | 3117 |
| 4 | L1 | 12.7 | 2 | 5.8 | 88.4 | 2.7 | 33 | 559 |
| 5 | L1 | 2.5 | 4 | 33.4 | 93.5 | 3.5 | 27 | 1721 |
| 6 | L1 | 3.5 | 4 | 28.1 | 93.8 | 3.4 | 28 | 1460 |
| 7 | L1 | 5.1 | 4 | 30.1 | 94.0 | 3.3 | 29 | 1545 |
| 8 | L1 | 12.7 | 4 | 4.1 | 86.1 | 2.6 | 33 | 194 |
| 9 | L2 | 5.1 | 2 | 2.6 | 85.4 | 3.1 | 28 | 245 |
| 10 | L2 | 12.7 | 2 | 1.8 | 78.7 | 2.7 | 30 | 154 |
| 11 | L3 | 5.1 | 2 | 65.5 | 93.9 | 3.6 | 26 | 6861 |
| 12 | L3 | 12.7 | 2 | 22.1 | 91.8 | 3.1 | 30 | 2302 |
| 13 | L3 | 12.7 | 4 | 21.5 | 91.5 | 3.1 | 30 | 1065 |
| 14 | L4 | 5.1 | 2 | 47.4 | 94.7 | 3.3 | 29 | 5022 |
| 15 | L4 | 12.7 | 2 | 15.8 | 93.7 | 3.0 | 32 | 1626 |
| 16 | L4 | 12.7 | 4 | 19.5 | 94.1 | 2.9 | 32 | 1004 |
| 17 | L5 | 5.1 | 2 | 35.5 | 93.5 | 3.7 | 26 | 3757 |
| 18 | L5 | 12.7 | 2 | 31.2 | 95.4 | 3.0 | 32 | 3312 |
| 19 | L5 | 12.7 | 4 | 29.8 | 95.3 | 3.0 | 32 | 1575 |
| 20 | L6 | 5.1 | 2 | 72.5 | 94.2 | 3.4 | 28 | 7498 |
| 21 | L6 | 12.7 | 2 | 76.6 | 95.0 | 3.4 | 28 | 7777 |
| 22 | L6 | 12.7 | 4 | 84.6 | 94.7 | 3.4 | 28 | 4299 |

[1]Catalyst efficiency = (grams of MOD-1)/(grams of Pd)/(hours of reaction time).

Data in Table 6 above show that each catalyst of the phosphine ligand L1 through L6 produces, under the reaction conditions described hereinabove, a product mixture with a catalyst efficiency at least 150 g of MOD-1 per g Pd per hour and a MOD-1 to MOD-3 molar ratio of 25/1 or higher. Furthermore, these palladium catalysts are more efficient when the initial concentration of methanol in the reaction fluid is 5.1 mol/liter than when it is 12.7 mol/liter.

Ex 23 and 24

Replicate Ex 4 (Pd-L1 catalyst stock solution, methanol concentration of 12.7 moles/liter and reaction time of 2 hours), except that additional amounts of L1 are added into the reaction solutions of Ex 23 and 24 to provide L1/Pd molar ratios of 5 and 30, respectively. Obtain GC data from each example and carry out calculations according to the equations described hereinabove. Table 7 shows the calculated results. The results from example 4 are reproduced here for easy comparison.

TABLE 7

Results from examples 20 and 21.

| Ex No. | L1/Pd Mol/mol | Conv (mol %) | MOD-1 (mol %) | MOD-3 (mol %) | L/B ratio | Catalyst efficiency[1] |
|---|---|---|---|---|---|---|
| 4 | 2 | 5.8 | 88.4 | 2.7 | 33 | 559 |
| 23 | 5 | 7.2 | 90.3 | 2.6 | 35 | 708 |
| 24 | 30 | 24.3 | 94.4 | 3.0 | 32 | 2546 |

[1]Catalyst efficiency = (grams of MOD-1)/(grams of Pd)/(hours of reaction time).

The data in Table 7 show that higher L1/Pd ratios (e.g., 30) lead to higher butadiene conversion, which can be interpreted as a result of stabilization of the Pd catalyst for a longer period of time by the additional amounts of the L1. The reaction conditions of all three examples are essentially the same except the L1/Pd ratios.

COMPARATIVE EXAMPLES

CEx

Carry out butadiene telomerization reactions using the catalyst stock solutions of the four (4) comparative ligands shown in Table 2 hereinabove.

CEx 1-6

Replicate Ex 2, 3, 4, 6, 7 and 8 hereinabove using the Pd-CL1 catalyst stock solution.

CEx 7-9

Replicate Ex 3, 4, and 8 hereinabove using the Pd-CL2 catalyst stock solution.

CEx 10-12

Replicate Ex 3, 4, and 8 hereinabove using the Pd-CL3 catalyst stock solution.

CEx 13 and 14

Replicate Ex 3 and 4 hereinabove using the Pd-CL4 catalyst stock solution.

Obtain GC data from each comparative example and carry out calculations according to the equations described hereinabove. Table 8 shows the calculated results from CEx 1-14.

TABLE 8

CEx using comparative ligands

| CEx No. | Ligand No. | [MeOH] (M) | RXT (far) | Conv (mol %) | MOD-1 (mol %) | MOD-3 (mol %) | L/B ratio | Catalyst efficiency[1] |
|---|---|---|---|---|---|---|---|---|
| 1 | CL1 | 3.7 | 2 | 31.7 | 76.5 | 5.4 | 14 | 2633 |
| 2 | CL1 | 5.1 | 2 | 39.1 | 73.5 | 4.3 | 17 | 3032 |
| 3 | CL1 | 12.7 | 2 | 78.7 | 89.2 | 4.6 | 20 | 7370 |
| 4 | CL1 | 3.7 | 4 | 42.3 | 72.3 | 4.8 | 15 | 1650 |
| 5 | CL1 | 5.1 | 4 | 63.6 | 77.9 | 5.3 | 15 | 2660 |
| 6 | CL1 | 12.7 | 4 | 83.2 | 89.6 | 4.5 | 20 | 4063 |
| 7 | CL2 | 5.1 | 2 | 65.6 | 87.7 | 4.7 | 19 | 6354 |
| 8 | CL2 | 12.7 | 2 | 55.7 | 93.6 | 3.9 | 24 | 5707 |
| 9 | CL2 | 12.7 | 4 | 65.6 | 93.6 | 3.9 | 24 | 3363 |
| 10 | CL3 | 5.1 | 2 | 80.1 | 89.2 | 5.0 | 18 | 7619 |
| 11 | CL3 | 12.7 | 2 | 76.4 | 90.5 | 4.5 | 20 | 7595 |
| 12 | CL3 | 12.7 | 4 | 87.8 | 90.7 | 4.5 | 20 | 4447 |
| CE13 | CL4 | 5.1 | 2 | 1.0 | 9.5 | 0.2 | 47 | 11 |
| CE14 | CL4 | 12.7 | 2 | 0.5 | 6.0 | 0.8 | 8 | 3 |

[1]Catalyst efficiency = (grams of MOD-1)/(grams of Pd)/(hours of reaction time).

The data in Table 8 show that the Pd catalysts of CL1-CL3 produce MOD-1/MOD-3 molar ratios of 24/1 or less, while Pd catalysts of CL4 has very low catalyst efficiency and produces MOD-1/MOD-3 molar ratios highly dependent on reaction conditions.

What is claimed is:

1. An improved process for telomerizing butadiene, the process comprising contacting butadiene and an organic hydroxy compound represented by formula ROH (I), wherein R is a substituted or unsubstituted $C_1$-$C_{20}$-hydrocarbyl and the organic hydroxy compound is not glycerol, in a reaction fluid in the presence of a palladium catalyst and a phosphine ligand, the improvement comprising, a) the phosphine ligand being selected from a group represented by formula (II):

$$P{-}\left[\begin{array}{c} \text{phenyl ring with H, } R^4, R^3, R^2, R^1 \end{array}\right]_3 \quad (II)$$

wherein:

$R^1$, $R^2$, $R^3$ and $R^4$ are each independently selected from the group consisting of hydrogen, halogen, substituted and unsubstituted $C_1$-$C_{20}$-hydrocarbyls, and substituted and unsubstituted $C_1$-$C_{20}$-hydrocarbyloxyls, provided that at least two $R^1$ moieties are independently selected from substituted and unsubstituted $C_1$-$C_{20}$-hydrocarbyloxyls and that the phosphine ligand has a total of two (2), three (3), four (4), five (5), or six (6) substituted or unsubstituted $C_1$-$C_{20}$-hydrocarbyloxyls;

wherein optionally on each phenyl ring, $R^1$ is bonded to $R^2$ to form a 5- to 7-membered ring, $R^2$ is bonded to $R^3$ to form a 5- to 7-membered ring, or $R^3$ is bonded to $R^4$ to form a 5- to 7-membered ring; and b) which contacting occurs in a reaction fluid, which reaction fluid comprises the butadiene, the organic hydroxy compound, the palladium catalyst, and the phosphine ligand, under conditions and for a reaction time sufficient to yield a product mixture comprising a linear product 1-RO-2,7-octadiene and a branched product 3-RO-1,7-octadiene with a linear product to branched product molar ratio of greater than 25/1 and a catalyst efficiency at least 150 grams of the linear product per gram palladium per hour, wherein R is as defined above.

2. The process of claim 1, wherein the phosphine ligand is selected from tris-(2-methoxyphenyl)phosphine, tris-(2,4-dimethoxyphenyl)phosphine, bis-(2-methoxyphenyl)phenylphosphine, tris-(2-methoxy-4-fluorophenyl)phosphine, and tris-(2-methoxy-4-chlorophenyl)phosphine.

3. The process of claim 1, wherein the organic hydroxy compound is fed into the reaction fluid in an amount sufficient to provide a concentration of the organic hydroxy compound in a range from 1.0 to 6.0 moles per liter of the reaction fluid.

4. The process of any one of claim 1, wherein the reaction fluid comprises from 1 to 100 parts per million palladium by weight based on the weight of the reaction fluid.

5. The process of any one of claim 1, wherein the reaction fluid comprises from 1.0 to 50 moles of the phosphine ligand per mole of palladium.

6. The process of any one of claim 1, further comprising a catalyst promoter having a $pK_b$ of greater than 5, the catalyst promoter being selected from a group consisting of tertiary amines, alkali metal borohydrides, oxides, and compounds having a generic formula $(R^5O^-)_n M^{n+}$, wherein $R^5$ is hydrogen, or a substituted or unsubstituted $C_{1-20}$ hydrocarbyl, M is an alkali metal, alkaline earth metal or quaternary ammonium, and n is 1 or 2.

7. The process of claim 6, wherein the catalyst promoter is employed in an amount from 0.01 to 1000 moles per mole of palladium.

8. The process of any one of claim 1, further comprising an organic solvent in an amount from 20% by weight to 80% by weight based on the weight of the reaction fluid.

9. The process of claim 8, wherein the organic solvent is selected from the group consisting of $C_4$-$C_{12}$ alkanes, $C_4$-$C_{12}$ alkenes, $C_6$-$C_{12}$ arenes, $C_4$-$C_{12}$ ethers, $C_5$-$C_{12}$ tertiary amines, and mixtures thereof.

10. The process of claim 1, further comprising the steps of:
(a) hydrogenating the product mixture under hydrogenation conditions effective to produce hydrogenation products comprising 1-RO-octane; and
(b) eliminating the RO— group from the hydrogenation products under elimination conditions effective to produce elimination products comprising 1-octene.

* * * * *